United States Patent
O'Rear et al.

(10) Patent No.: US 6,441,263 B1
(45) Date of Patent: Aug. 27, 2002

(54) ETHYLENE MANUFACTURE BY USE OF MOLECULAR REDISTRIBUTION ON FEEDSTOCK $C_{3-5}$ COMPONENTS

(75) Inventors: Dennis J. O'Rear, Petaluma, CA (US); Rodney Porter, Pearland, TX (US); Cong-Yan Chen, Kensington, CA (US)

(73) Assignee: ChevronTexaco Corporation, San Ramon, CA (US)

(*) Notice: Subject to any disclaimer, the term of this patent is extended or adjusted under 35 U.S.C. 154(b) by 0 days.

(21) Appl. No.: 09/612,045

(22) Filed: Jul. 7, 2000

(51) Int. Cl.[7] .................................................. C07C 4/02

(52) U.S. Cl. .................... 585/650; 585/646; 585/647; 585/643; 585/324; 585/648; 208/66

(58) Field of Search ........................ 585/324, 648, 585/650, 646, 647, 643; 208/66

(56) References Cited

U.S. PATENT DOCUMENTS

| | | | |
|---|---|---|---|
| 2,573,341 A | * 10/1951 | Kniel | ............ 585/650 |
| 2,882,244 A | 4/1959 | Milton | |
| 3,130,007 A | 4/1964 | Breck | |
| 3,216,789 A | 11/1965 | Breck et al. | |
| 3,415,736 A | 12/1968 | Ciric | |
| 3,415,737 A | 12/1968 | Kluksdahl | |
| 3,485,890 A | * 12/1969 | Dixon | ............ 585/251 |
| 3,546,102 A | 12/1970 | Bertolacini | |
| 3,574,092 A | 4/1971 | Mitsche | |
| 3,668,268 A | 6/1972 | Mulaskey | |
| 3,679,575 A | 7/1972 | Bertolacini | |
| 3,692,470 A | 9/1972 | Ciric | |
| 3,709,979 A | 1/1973 | Chu | |
| 3,832,449 A | 8/1974 | Rosinski et al. | |
| 3,852,207 A | 12/1974 | Stangeland et al. | |
| 3,856,876 A | * 12/1974 | Burnett | ............ 585/708 |
| RE28,341 E | 2/1975 | Wadlinger et al. | |
| 3,904,513 A | 9/1975 | Fischer et al. | |
| 3,972,983 A | 8/1976 | Ciric | |
| 4,016,245 A | 4/1977 | Plank et al. | |
| 4,018,711 A | 4/1977 | Bertolacini | |
| 4,076,842 A | 2/1978 | Plank et al. | |

(List continued on next page.)

FOREIGN PATENT DOCUMENTS

| | | |
|---|---|---|
| EP | 0 358 915 A2 | 2/1990 |
| EP | 0 421 700 A1 | 4/1991 |
| EP | 0 498 182 A1 | 8/1992 |
| GB | 1117568 | 6/1968 |

OTHER PUBLICATIONS

Trends in NGL Recovery from Natural and Associated Gases, C. Collinc et al., GasTech LNG/LPG Conference, Nov. 6–9, 1984, pp. 287–303.

Catalytic Reforming, Donald M. Little, PennWell Books, 1985, in its entirety. no month.

Petroleum & Petrochemical International, vol. 12, No. 12, pp. 65 to 68. no date.

*Primary Examiner*—Nadine Preisch
(74) *Attorney, Agent, or Firm*—Burns, Doane, Swecker & Mathis, L.L.P.

(57) ABSTRACT

A process for preparing an ethylene-rich composition from a $C_{3-5}$ paraffinic feedstock is described. The $C_{3-5}$ paraffinic feedstock is subjected to molecular redistribution via dehydrogenation to form olefins, metathesis of the olefins, and rehydrogenation of the olefins to form paraffins. The product stream includes ethane, which is isolated and sent to an ethane or ethane/propane cracker (or, alternatively, a flexicracker, although this is less cost effective) to yield an ethylene-rich composition. The product stream also includes $C_{3-5}$ paraffins, which can be recycled, and $C_6$+paraffins, which can be used, for example, as solvents. Alternatively, they can be isomerized to form gasoline additives, or can be converted to aromatic compounds by subjecting them to reforming conditions, for example using the AROMAX™ process or platforming or rheniforming conditions.

21 Claims, 4 Drawing Sheets

U.S. PATENT DOCUMENTS

| | | | |
|---|---|---|---|
| 4,104,320 | A | 8/1978 | Bernard et al. |
| RE29,948 | E | 3/1979 | Dwyer et al. |
| 4,157,294 | A | 6/1979 | Iwao et al. |
| 4,241,036 | A | 12/1980 | Flanigen et al. |
| 4,347,121 | A | 8/1982 | Mayer et al. |
| 4,347,394 | A | 8/1982 | Detz et al. |
| 4,370,224 | A | 1/1983 | Eberly, Jr. et al. |
| 4,401,556 | A | 8/1983 | Bezman et al. |
| 4,417,083 | A | 11/1983 | Bernard et al. |
| 4,434,311 | A | 2/1984 | Buss et al. |
| 4,440,871 | A | 4/1984 | Lok et al. |
| 4,447,316 | A | 5/1984 | Buss |
| 4,456,527 | A | 6/1984 | Buss et al. |
| 4,499,327 | A | 2/1985 | Kaiser |
| 4,500,651 | A | 2/1985 | Lok et al. |
| 4,530,824 | A | 7/1985 | Arika et al. |
| 4,534,853 | A | 8/1985 | Long et al. |
| 4,544,143 | A | 10/1985 | Cooper et al. |
| 4,544,539 | A | 10/1985 | Wortel |
| 4,552,731 | A | 11/1985 | Vaughan |
| 4,556,477 | A | 12/1985 | Dwyer |
| 4,567,029 | A | 1/1986 | Wilson et al. |
| 4,585,747 | A | 4/1986 | Valyocsik |
| 4,634,518 | A | 1/1987 | Buss et al. |
| 4,663,493 | A * | 5/1987 | Vora et al. ............ 585/655 |
| 4,677,237 | A * | 6/1987 | Imai et al. ............ 585/444 |
| 4,681,865 | A | 7/1987 | Katsuno et al. |
| 4,686,093 | A | 8/1987 | Flanigen et al. |
| 4,761,512 | A | 8/1988 | Katsuno et al. |
| 4,810,357 | A | 3/1989 | Chester et al. |
| 4,820,402 | A | 4/1989 | Partidge et al. |
| 4,827,667 | A | 5/1989 | Jarvis |
| 4,834,977 | A | 5/1989 | Kohama et al. |
| 4,859,422 | A | 8/1989 | Qureshi et al. |
| 4,861,743 | A | 8/1989 | Flank et al. |
| 4,910,006 | A | 3/1990 | Zones et al. |
| 4,913,799 | A | 4/1990 | Gortsema et al. |
| 4,963,337 | A | 10/1990 | Zones |
| 4,973,785 | A | 11/1990 | Lok et al. |
| 5,026,935 | A * | 6/1991 | Leyshon et al. ............ 585/315 |
| 5,053,373 | A | 10/1991 | Zones |
| 5,059,567 | A | 10/1991 | Linsten et al. |
| 5,073,530 | A | 12/1991 | Bezman et al. |
| 5,073,652 | A | 12/1991 | Katsuno et al. |
| 5,082,481 | A | 1/1992 | Barches et al. |
| 5,091,351 | A | 2/1992 | Murakawa et al. |
| 5,106,801 | A | 4/1992 | Zones et al. |
| 5,114,563 | A | 5/1992 | Lok et al. |
| 5,158,665 | A | 10/1992 | Miller |
| 5,198,203 | A | 3/1993 | Kresge et al. |
| 5,200,377 | A | 4/1993 | Zones et al. |
| 5,202,014 | A | 4/1993 | Zones et al. |
| 5,246,689 | A | 9/1993 | Beck et al. |
| 5,254,514 | A | 10/1993 | Nakagawa |
| 5,254,781 | A * | 10/1993 | Calamur et al. ............ 585/500 |
| 5,316,753 | A | 5/1994 | Nakagawa |
| 5,334,368 | A | 8/1994 | Beck et al. |
| 5,354,933 | A | 10/1994 | Ohashi et al. |
| 5,437,855 | A | 8/1995 | Valyocsik |
| 5,452,581 | A | 9/1995 | Dinh |
| 5,476,978 | A | 12/1995 | Smith, Jr. et al. |
| 5,491,119 | A | 2/1996 | Verduijn |
| 5,514,362 | A | 5/1996 | Miller |
| 5,558,851 | A | 9/1996 | Miller |
| 5,559,068 | A | 9/1996 | Chen et al. |
| 5,580,540 | A | 12/1996 | Nakagawa |
| 5,591,421 | A | 1/1997 | Zones |
| 5,624,657 | A | 4/1997 | Vaughan |
| 5,634,354 | A | 6/1997 | Howard et al. |
| 5,653,956 | A | 8/1997 | Zones |
| 5,685,973 | A | 11/1997 | Zones et al. |
| 5,770,175 | A | 6/1998 | Zones |
| 5,846,400 | A | 12/1998 | Zones et al. |
| 5,939,044 | A | 8/1999 | Nakagawa et al. |
| 5,960,643 | A | 10/1999 | Kuechler et al. |
| 5,990,360 | A | 11/1999 | Burdet et al. |
| 6,225,359 | B1 * | 5/2001 | O'Rear et al. ............ 518/706 |

* cited by examiner

ETHYLENE MANUFACTURE BY USE OF MOLECULAR REDISTRIBUTION ON FEEDSTOCK $C_{3-5}$ COMPONENTS

FIELD OF THE INVENTION

This invention relates to the production of ethylene from a predominantly $C_{3-5}$-paraffinic feedstock.

BACKGROUND OF THE INVENTION

Ethylene is a commonly used feedstock and is used to form a variety of end and intermediate products, including ethylene oxide, ethyl acetate, and ethylene polymers and copolymers. The polymers are used to form a variety of plastics, resins fibers, and the like. Ethylene is one of the leading petrochemicals in terms of production volume, sales value and number of derivatives. An estimated 76 million tons were produced in 1995 alone, and a roughly three percent increase per year is expected. It will be difficult to meet the needs for ethylene in the future with existing methodologies.

There are several commercial methods for generating ethylene. One method under development involves the conversion of methanol to olefins (see, for example, U.S. Pat. No. 4,499,327 to Kaiser). Ethylene has been prepared from oxygenated materials, for example, alcohols, by converting the oxygenated materials to olefins, and metathesizing olefins such as propylene to produce ethylene. See, for example, U.S. Pat. No. 5,990,360 to Barger et al. A limitation of this approach is that oxygenated materials are a relatively expensive feedstock for use in preparing ethylene.

The main commercial methods involve hydrocarbon pyrolysis, also known as steam cracking. This technique can use a number of different hydrocarbon feedstocks. When ethane is the feed, an ethane cracker can be used. This technique is the least capital intensive and provides the fewest by-products. When the feed includes a mixture of ethane and propane, a more capital-intensive ethane-propane (EP) cracker is needed. When the feed includes a mixture of ethane to pentane, a still more capital-intensive flexi-cracker is needed. Accordingly, it is desirable to provide feedstocks that are rich in ethane, and possibly include propane, but preferably which do not include appreciable amounts of butane, pentane or higher molecular weight paraffins.

An example of a process using a less desirable feed for the cracking reaction is shown in U.S. Pat. No. 5,026,935 to Leyshon et al. Leyshon et al. disclose a process for preparing ethylene from butanes or higher molecular weight feedstocks via cracking and metathesis to form ethylene and propylene. At least a portion of the propylene is metathesized to ethylene. The method is relatively expensive because it requires using relatively expensive cracking conditions, and because it makes the overall efficiency and yield relatively low.

It would be desirable to provide a process for producing ethylene that does not require using a Flexicracker, using oxygenated feedstocks, or cracking significant amounts of relatively high molecular weight (i.e., $C_4+$) products. The present invention provides such a process.

SUMMARY OF THE INVENTION

In its broadest aspect, the present invention is directed to an integrated process for producing ethylene or a mixture of ethylene and propylene from a feedstock that includes $C_{3-5}$ paraffins. The process involves obtaining an appropriate $C_{3-5}$-containing feedstock and subjecting the paraffins to conditions of molecular redistribution. During the course of this reaction, the feedstock undergoes a series of reactions involving paraffin dehydrogenation to form olefins, olefin metathesis, and olefin rehydrogenation to form paraffins. The molecular redistribution reaction provides a product stream that includes $C_2$ and $C_6+$paraffins, in addition to $C_{3-5}$ paraffins.

The product stream can be distilled to provide a first fraction rich in either ethane or a mixture of ethane and propane, depending on the type of distillation apparatus, a second fraction rich in unconverted $C_{3-5}$ paraffins and a third fraction containing predominantly $C_6+$paraffins. The $C_2$ stream can be sent to an ethane cracker to provide ethylene, or, alternatively, the $C_{2-3}$ fraction can be sent to an ethane/propane (EP) cracker to provide ethylene and propylene. The $C_{3-5}$ fraction can be recycled through the molecular redistribution stage to provide additional ethane, propane and $C_6+$paraffins.

The $C_6+$fraction from the molecular redistribution step tends to have low ppb sulfur, and can be used, for example, as a solvent, or as a feedstock for reforming processes to form aromatic compounds, for example the AROMAX™ process or platforming or rheniforming processes. The products may also optionally be isomerized to increase their octane value, and the isomerized products can be used in gasoline compositions.

Depending on the nature of the molecular redistribution chemistry, the feedstock may not be able to include appreciable amounts (i.e., amounts that would adversely affect the catalyst used for molecular redistribution) of hydrogen, olefins, alkynes, thiols, amines, water, air, oxygenates or cycloparaffins.

Methane does not participate in the reaction (it cannot be dehydrogenated to form an olefin) but does dilute the reactants and may be required to be removed from the feedstock to improve the throughput of the reaction. Because the molecular redistribution reaction proceeds toward a thermodynamic equilibrium, the presence of ethane in the feedstock should be minimized, as it will limit conversion of $C_{3-5}$ paraffins to ethane.

Hydrogen, water, air, methane and ethane can be removed from feedstocks using conventional methodology, for example using demethanizer and deethanizer columns. Methods for removing sulfur, oxygenates and nitrogen compounds are well known, and generally involve hydrotreating the feedstock. Methods for removing cyclic compounds are also known in the art and generally involve adsorption and separation by molecular sieves.

Refinery waste gas predominantly includes hydrogen and $C_{1-5}$ paraffins, but may include small amounts of olefins and alkynes, as well as heteroatom-containing impurities. Natural gas predominantly includes $C_{1-5}$ paraffins, but may include sulfur and nitrogen impurities. Cracked gas feedstreams predominantly include hydrogen and $C_{1-6}$ paraffins, olefins, alkynes and sulfur and nitrogen impurities. The hydrogen, methane, ethane and heteroatom-containing impurities from these feedstocks are removed, and any olefins and/or alkynes hydrogenated, before the feedstocks are used in the processes described herein. LPG, derived from petroleum refining, contains mostly propane and butanes, with small amounts of pentane, and does not need to be demethanized and/or deethanized, but may need to be treated to remove impurities such as cycloparaffins and sulfur and nitrogen compounds.

DETAILED DESCRIPTION OF THE INVENTION

Figure 1:
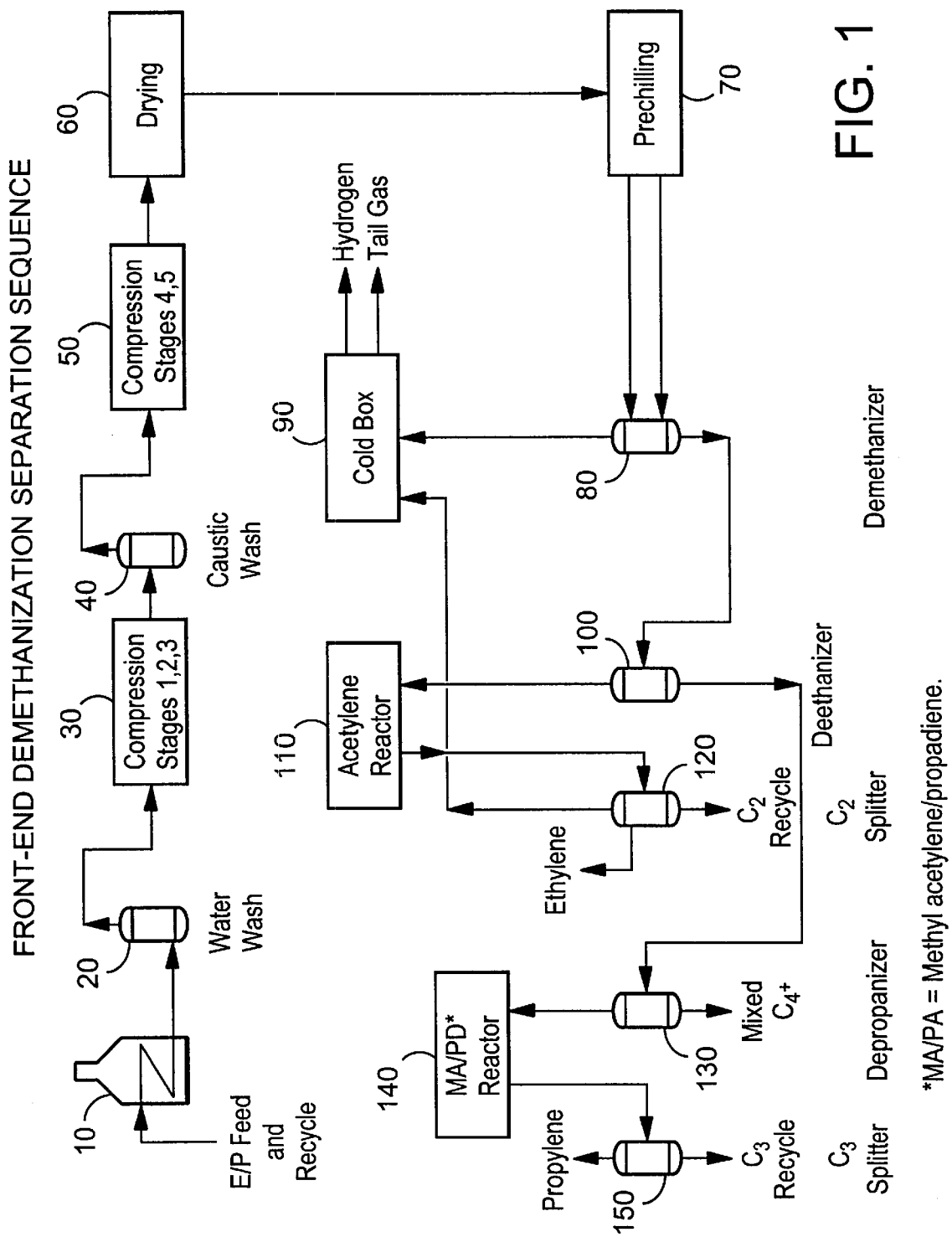
FIG. 1 is a schematic flow diagram representing a front-end demethanization process.

In its broadest aspect, the present invention is directed to an integrated process for producing ethylene-rich and, optionally, propylene-rich product streams from a feedstock that includes $C_{3-5}$ paraffins. The process involves obtaining an appropriate $C_{3-5}$-containing paraffinic feedstock and subjecting it to molecular redistribution, which involves paraffin dehydrogenation to form olefins, olefin metathesis, and olefin rehydrogenation to form paraffins. At least a portion of the initial $C_{3-5}$ paraffins is converted to ethane and $C_6$+paraffins. Unconverted $C_{3-5}$ paraffins can be recycled if desired and converted to additional ethane and $C_6$+paraffins.

The process described herein is an integrated process. As used herein, the term "integrated process" refers to a process which involves a sequence of steps, some of which may be parallel to other steps in the process, but which are interrelated or somehow dependent upon either earlier or later steps in the total process.

An advantage of the present process is the effectiveness and relatively inexpensive processing costs with which the present process may be used to prepare high quality ethylene or ethylene/propylene. In particular, an advantage is that feedstocks that are not conventionally recognized as suitable sources for such product streams can be used.

I. Preparation of Feedstocks for the Molecular Redistribution Reaction

Feedstocks for the Molecular Redistribution Reaction

Examples of feedstocks that can be molecularly subjected to molecular redistribution in accordance with the present invention include process streams that include paraffins in the $C_{3-5}$ range. Numerous petroleum feedstocks, for example those derived from crude oil and natural gas, are suitable for use. Any feedstock that includes $C_{3-5}$ paraffins and which does not include an appreciable amount of methane, ethane, olefins, alkynes, cycloparaffins, and heteroatom-containing compounds can be used. Suitable feedstocks can be derived from natural gas, cracked gas feed streams, LPG and refinery waste gas by removing the bulk of the above-listed compounds from the feedstock.

The preferred feedstock is derived from natural gas. In addition to methane, natural gas includes some heavier hydrocarbons ($C_{2-5}$ paraffins) and other impurities, e.g., carbon dioxide, nitrogen, helium, water and non-hydrocarbon acid gases. The methane, ethane, and various impurities are removed to provide a feedstock rich in $C_{3-5}$ paraffinic hydrocarbons. The nitrogen and helium can be tolerated. They are like methane in that they are inert and may reduce the conversion of paraffins in the feed.

LPG, derived from petroleum refining, contains mostly propane and butanes, with small amounts of pentane. Depending on the exact nature of the source, it can include heteroatom-containing impurities. It can typically be used without further treatment, provided it does not include appreciable amounts of cycloparaffins, or heteroatom-containing compounds.

Cracked gas feedstreams include hydrogen and $C_{1-6}$ paraffins. Refinery waste gas includes hydrogen and $C_{1-5}$ paraffins. These streams must be treated to remove hydrogen, methane and ethane, as well as any olefins, alkynes, cycloparaffins, or heteroatom-containing compounds. For this reason, they are less preferred feedstocks.

Removal of Hydrogen and Methane from the Feedstock

Methods for removing methane from an paraffin fraction are well known to those of skill in the art. Suitable methods include absorption, refrigerated absorption, .adsorption and condensation at cryogenic temperatures down to about −175° F.

Demethanizers and other means for removing methane are well known to those of skill in the art, and are described, for example, in U.S. Pat. No. 5,960,643 to Kuechler et al. and C. Collins, R. J. J. Chen and D. G. Elliot, "Trends in NGL Recovery for Natural and Associated Gases", GasTech, Ltd. of Rickmansworth, England, pages 287–303, GasTech LNG/LPG Conference 84, the contents of which are hereby incorporated by reference.

$C_2$+paraffins can typically be separated from methane to provide pipeline quality methane and recovered natural gas liquids. These natural gas liquids include ethane, propane, butane and other heavier hydrocarbons. In addition to these NGL components, other gases, including hydrogen, ethylene and propylene, may be contained in gas streams from refinery or petrochemical plants. Hydrogen can be removed using conventional methods or, optionally, used to hydrogenate any olefins and/or alkynes present in the feedstock, before the molecular redistribution step.

Demethanizer columns, which include one or more distillation towers, are typically used to separate methane and other more volatile components from ethane and less volatile components. High pressure demethanizers typically operate at pressures higher than 2.758 MPa (400 psi) and can produce overhead reflux by condensation against a pure component ethylene refrigeration. Demethanizer overhead temperatures of these systems are typically in the range of −85° C. to −100° C. Ethylene refrigeration at approximately −101° C. is typically used for chilling the overhead condenser. At pressures below 2.758 MPa, the overhead temperature is typically too low to use ethylene refrigeration unless a vacuum suction is used. However, that is not preferable due to potential air leakage into the system.

Hydrogen can be removed from the feedstock using methods which are well known in the art, and which are described, for example, in U.S. Pat. Nos. 5,082,481, 5,452,581, and 5,634,354, the contents of which are hereby incorporated by reference. These methods typically involve using a membrane separator to remove hydrogen from the feedstock.

Deethanization

The molecular redistribution reaction, involving paraffin dehydrogenation, olefin metathesis, and olefin hydrogenation proceeds toward a roughly thermodynamic equilibrium of the mixture of products. For this reason, the majority of the ethane in the feedstock is preferably removed before the molecular redistribution step. Methods for removing ethane from an paraffin fraction are well known to those of skill in the art, and generally involve using a deethanizer. Ethane is preferably separated from propane and less volatile components. The ethane can be sent to directly to an ethane cracker to form ethylene.

In some embodiments, the ethane stream includes appreciable amounts of propane. The resulting ethane/propane mixture can be sent directly to an ethane/propane cracker to form ethylene and propylene.

In other embodiments, the ethane contains appreciable amounts of methane. While this ethane-rich stream can be sent to an ethane cracker, the ethylene formed in the ethane cracker needs to be separated from the methane. Methods for separating methane from ethylene are well known to those of skill in the art. However, it is preferred that the methane is separated from the ethane before the ethane is sent to the ethane cracker.

De-sulfuration and De-nitrification Chemistry

As noted above, the feedstocks may need to exclude appreciable amounts of heteroatoms or saturated $C_6$ cyclic compounds, depending on the catalysts used for the molecular redistribution reaction. If any heteroatoms or saturated cyclic compounds are present in the feedstock, they may need to be removed before the molecular redistribution reaction.

Saturated and partially saturated cyclic hydrocarbons (cycloparaffins, aromatic-cycloparaffins, and alkyl derivatives of these species) can form hydrogen during the molecular redistribution reaction. This hydrogen can inhibit the reaction, and should therefore be substantially excluded from the feed. The desired paraffins can be separated from the saturated and partially saturated cyclic hydrocarbons by using molecular sieve adsorbents or other techniques well known in the art.

Sulfur impurities can be removed using means well known to those of skill in the art, for example extractive Merox, hydrotreating, adsorption, etc. Nitrogen-containing impurities can also be removed using means well known to those of skill in the art. Hydrotreating is the preferred means for removing these and other impurities.

Accordingly, it may be preferred that the feedstocks be hydrotreated before performing the molecular redistribution process described herein. As used herein, the term "hydrotreating" is given its conventional meaning and describe processes that are well known to those skilled in the art. Hydrotreating refers to a catalytic process, usually carried out in the presence of free hydrogen, in which the primary purpose is the desulfurization and/or denitrification of the feedstock. The sulfur is generally converted to hydrogen sulfide, and the nitrogen is generally converted to ammonia, and these can be removed from the product stream using means well known to those of skill in the art.

Generally, in hydrotreating operations, cracking of the hydrocarbon molecules, i.e., breaking the larger hydrocarbon molecules into smaller hydrocarbon molecules, is minimized and the unsaturated hydrocarbons are either fully or partially hydrogenated.

Catalysts used in carrying out hydrotreating operations are well known in the art. See, for example, U.S. Pat. Nos. 4,347,121 and 4,810,357 for general descriptions of hydrotreating, and typical catalysts used hydrotreating processes.

Suitable catalysts include noble metals from Group VIIIA, such as platinum or palladium on an alumina or siliceous matrix, and unsulfided Group VIIIA and Group VIB metals, such as nickel-molybdenum or nickel-tin on an alumina or siliceous matrix. U.S. Pat. No. 3,852,207 describes a suitable noble metal catalyst and reaction conditions. Other suitable catalysts are described, for example, in U.S. Pat. Nos. 4,157,294 and 3,904,513. Non-noble metals (such as nickel-molybdenum) are usually present in the final catalyst composition as oxides, or possibly as sulfides, when such compounds are readily formed from the particular metal involved. Preferred non-noble metal catalyst compositions contain in excess of about 5 weight percent, preferably about 5 to about 40 weight percent molybdenum and/or tungsten, and at least about 0.5, and generally about 1 to about 15 weight percent of nickel and/or cobalt determined as the corresponding oxides. The noble metal (such as platinum) catalysts include in excess of 0.01 percent metal, preferably between 0.1 and 1.0 percent metal. Combinations of noble metals may also be used, such as mixtures of platinum and palladium.

The hydrogenation components can be incorporated into the overall catalyst composition by any one of numerous procedures. The hydrogenation components can be added to matrix component by co-mulling, impregnation, or ion exchange and the Group VI components, i.e., molybdenum and tungsten can be combined with the refractory oxide by impregnation, co-mulling or co-precipitation. Although these components can be combined with the catalyst matrix as the sulfides, that may not be preferred, as the sulfur compounds may interfere with some molecular redistribution catalysts.

The matrix component can be of many types including some that have acidic catalytic activity. Ones that have activity include amorphous silica-alumina or may be a zeolitic or non-zeolitic crystalline molecular sieve. Examples of suitable matrix molecular sieves include zeolite Y, zeolite X and the so-called ultra stable zeolite Y and high structural silica:alumina ratio zeolite Y such as that described in U.S. Pat. Nos. 4,401,556, 4,820,402 and 5,059,567. Small crystal size zeolite Y, such as that described in U.S. Pat. No. 5,073,530, can also be used. Non-zeolitic molecular sieves which can be used include, for example, silicoaluminophosphates (SAPO), ferroaluminophosphate, titanium aluminophosphate, and the various ELAPO molecular sieves described in U.S. Pat. No. 4,913,799 and the references cited therein. Details regarding the preparation of various non-zeolite molecular sieves can be found in U.S. Pat. Nos. 5,114,563 (SAPO); 4,913,799 and the various references cited in U.S. Pat. No. 4,913,799. Mesoporous molecular sieves can also be used, for example the M41S family of materials (*J. Am. Chem. Soc.* 1992, 114, 10834–10843), MCM-41 (U.S. Pat. Nos. 5,246, 689, 5,198, 203 and 5,334,368), and MCM48 (Kresge et al., *Nature*359 (1992) 710).

Suitable matrix materials may also include synthetic or natural substances as well as inorganic materials such as clay, silica and/or metal oxides such as silica-alumina, silica-magnesia, silica-zirconia, silica-thoria, silica-berylia, silica-titania as well as ternary compositions, such as silica-alumina-thoria, silica-alumina-zirconia, silica-alumina-magnesia, and silica-magnesia zirconia. The latter may be either naturally occurring or in the form of gelatinous precipitates or gels including mixtures of silica and metal oxides. Naturally occurring clays which can be composited with the catalyst include those of the montmorillonite and kaolin families. These clays can be used in the raw state as originally mined or initially subjected to calumniation, acid treatment or chemical modification.

Furthermore, more than one catalyst type may be used in the reactor. The different catalyst types can be separated into layers or mixed. Typical hydrotreating conditions vary over a wide range. In general, the overall LHSV is about 0.25 to 2.0, preferably about 0.5 to 1.0. The hydrogen partial pressure is greater than 200 psia, preferably ranging from about 500 psia to about 2000 psia. Hydrogen recirculation rates are typically greater than 50 SCF/Bb1, and are preferably between 1000 and 5000 SCF/Bb1. Temperatures range from about 300° F. to about 750° F., preferably ranging from 450° F. to 600° F.

The contents of each of the patents and publications referred to above are hereby incorporated by reference in its entirety.

II. Molecular Redistribution Chemistry

As used herein, "molecular redistribution" is a process in which a paraffin is converted into a mixture of lighter and heavier paraffins. The term "disproportionation" is also used herein to describe these processes.

Molecular redistribution typically uses a combination of conventional hydrogenation/dehydrogenation catalysts, such as $Pt/Al_2O_3$, and conventional olefin metathesis catalysts, such as $W/SiO_2$ (or inexpensive variations thereof). The chemistry does not require using hydrogen gas, and therefore does not require relatively expensive recycle gas compressors. The chemistry is typically performed at mild pressures (100–5000 psig). The chemistry is typically thermoneutral and, therefore, there is no need for additional equipment to control the temperature.

Depending on the nature of the catalysts, molecular redistribution may be sensitive to impurities in the feedstock, such as sulfur and nitrogen-containing compounds and moisture, and these may need to be removed prior to the reaction. The presence of excess olefins and hydrogen in the molecular redistribution zone are also known to affect the equilibrium of the molecular redistribution reaction and to deactivate the catalyst. Since the composition of the fractions may vary, some routine experimentation will be necessary to identify the contaminants that are present and identify the optimal processing scheme and catalyst to use in carrying out the invention.

Molecular redistribution, as described herein, generally involves two distinct chemical reactions. First, the paraffins are converted into olefins on the dehydrogenation/hydrogenation catalyst in a process known as dehydrogenation or unsaturation. The resulting olefins are disproportionated into lighter and heavier olefins by a process known as olefin metathesis upon contacting the metathesis catalyst. The metathesized olefins are then converted into paraffins in a process known as hydrogenation or saturation upon contact with the dehydrogenation/hydrogenation catalyst. The $C_{3-5}$-containing feedstock is subjected to molecular redistribution to produce a product stream that includes $C_2$ and $C_6$+hydrocarbons.

Various catalysts are known to catalyze the molecular redistribution reaction. The catalyst mass used to carry out the present invention must have both dehydrogenation/hydrogenation activity and olefin metathesis activity. The dehydrogenation activity is believed to be necessary to convert the paraffins to olefins, which are believed to be the actual species that undergo olefin metathesis. Following olefin metathesis, the olefin is converted back into an paraffin. It is theorized that the dehydrogenation/hydrogenation activity of the catalyst also contributes to rehydrogenation of the olefin to an paraffin. While it is not intended that the present invention be limited to any particular mechanism, it may be helpful in explaining the choice of catalysts to further discuss the sequence of chemical reactions which are believed to be responsible for molecular redistribution of the paraffins. As an example, the general sequence of reactions for $C_3$ paraffins is believed to be:

$$C_3H_8 \leftrightharpoons C_3H_6 + H_2$$

$$2C_3H_6 \leftrightharpoons C_2H_4 + C_4H_8$$

$$C_2H_4 + C_4H_8 + 2H_2 \leftrightharpoons C_2H_6 + C_4H_{10}$$

The molecular redistribution reaction uses different catalysts having separate dehydrogenation/hydrogenation and olefin metathesis activity, one to dehydrogenate the paraffinic feedstock and hydrogenate the metathesized olefins and the other to methathesize the (dehydrogenated) feedstock. The dehydrogenation/hydrogenation catalyst will typically include a Group VIII metal from the Periodic Table of the Elements, which includes iron, cobalt, nickel, palladium, platinum, rhodium, ruthenium, osmium, and iridium.

Platinum and palladium or the compounds thereof are preferred for inclusion in the dehydrogenation/hydrogenation component, with platinum or a compound thereof being especially preferred. As noted previously, when referring to a particular metal in this disclosure as being useful in the present invention, the metal may be present as elemental metal or as a compound of the metal. As discussed above, reference to a particular metal in this disclosure is not intended to limit the invention to any particular form of the metal unless the specific name of the compound is given, as in the examples in which specific compounds are named as being used in the preparations.

Usually, the olefin metathesis catalyst will include one or more of a metal or the compound of a metal from Group VIB or Group VIIB of the Periodic Table of the Elements, which include chromium, manganese, molybdenum, rhenium and tungsten. Molybdenum, rhenium, tungsten, and compounds including these metals are preferred for including in the molecular redistribution catalyst. Tungsten and compounds including tungsten are particularly preferred. The metals described above may be present as elemental metals or as compounds including the metals, such as, for example, metal oxides. The metals may be present on the catalyst component either alone or in combination with other metals.

In most cases, the metals in the catalyst mass will be supported on a refractory material. Refractory materials suitable for use as a support for the metals include conventional refractory materials used in the manufacture of catalysts for use in the refining industry. Such materials include, but are not necessarily limited to, alumina, zirconia, silica, boria, magnesia, titania and other refractory oxide material or mixtures of two or more of any of the materials. The support may be a naturally occurring material, such as clay, or synthetic materials, such as silica-alumina and borosilicates. Molecular sieves, such as zeolites, also have been used as supports for the metals used in carrying out the dual functions of the catalyst mass. See, for example, U.S. Pat. No. 3,668,268. Mesoporous materials such as MCM-41 and MCM-48, such as described in Kresge, C. T., et al., *Nature* (Vol. 359) pp. 710–712, 1992, may also be used as a refractory support. Other known refractory supports, such as carbon, may also serve as a support for the active form of the metals in certain embodiments. The support is preferably non-acidic, i.e., having few or no free acid sites on the molecule. Free acid sites on the support may be neutralized by means of alkali metal salts, such as those of lithium. Alumina, particularly alumina on which the acid sites have been neutralized by an alkali salt, such as lithium nitrate, is usually preferred as a support for the dehydrogenation/hydrogenation component, and silica is usually preferred as the support for the metathesis component. The amount of active metal present on the support may vary, but it must be at least a catalytically active amount, i.e., a sufficient amount to catalyze the desired reaction. In the case of the dehydrogenation/hydrogenation component, the active metal content will usually fall within the range from about 0.01 weight percent to about 50 weight percent on an elemental basis, with the range of from about 0.1 weight percent to about 20 weight percent being preferred. For the metathesis component, the active metals content will usually fall within the range of from about 0.01 weight percent to about 50 weight percent on an elemental basis, with the range of from about 0.1 weight percent to about 25 weight percent being preferred.

A typical catalyst for use in the processes described herein includes a platinum component and a tungsten component as described in U.S. Pat. No. 3,856,876, the entire disclosure of which is herein incorporated by reference. In one embodiment of the present invention, the catalyst includes a mixture of platinum-on-alumina and tungsten-on-silica, wherein the volumetric ratio of the platinum component to the tungsten component is greater than 1:50 and less than 50:1. Preferably, the volumetric ratio of the platinum component to the tungsten component in this particular embodiment is between 1:10 and 10:1. The percent of surface of the metals should be maximized with at least 10% of the surface metal atoms exposed to the reactant.

In one embodiment, both the dehydrogenation/hydrogenation component and the olefin metathesis component are present within the catalyst mass on the same support particle as, for example, a catalyst in which the dehydrogenation/hydrogenation component is dispersed on an unsupported olefin metathesis component such as tungsten oxide. However, in an alternative embodiment, the catalyst components are separated on different particles.

In a reactor having a layered fixed catalyst bed, the two components may, in such an embodiment, be separated in different layers within the bed. However, separate reactors may be used for carrying out the dehydrogenation and olefin metathesis steps. In processing schemes where the dehydrogenation of the paraffins to olefins occurs separately from the olefin metathesis reaction, it may be necessary to include an additional hydrogenation step in the process, since the rehydrogenation of the olefins must take place after the olefin metathesis step.

The process conditions selected for carrying out the present invention will depend upon the molecular redistribution catalysts used. In general, the temperature in the reaction zone will be within the range of from about 400° F. (200° C.) to about 1000° F. (540° C.) with temperatures in the range of from about 500° F. (260° C.) to about 850° F. (455° C.) usually being preferred. In general, the conversion of the paraffins increases with an increase in pressure. Therefore, the selection of the optimal pressure for carrying out the process will usually be at the highest practical pressure under the circumstances. Accordingly, the pressure in the reaction zone should be maintained above 100 psig, and preferably the pressure should be maintained above 500 psig. The maximum practical pressure for the practice of the invention is about 5000 psig. More typically, the practical operating pressure will below about 3000 psig. The feedstock to the molecular redistribution reactor should contain a minimum of olefins, and preferably should contain no added hydrogen.

Platinum/tungsten catalysts are particularly preferred for carrying out the present invention because the molecular redistribution reaction will proceed under relatively mild conditions. When using the platinum/tungsten catalysts, the temperature should be maintained within the range of from about 400° F. (200° C.) to about 1000° F. (540° C.), with temperatures above about 500° F. (260° C.) and below about 800° F. being particularly desirable.

The olefin metathesis reaction described above is reversible, which means that the reaction proceeds to an equilibrium limit. Therefore, if the feed to the molecular redistribution zone has two streams of paraffins at different molecular weights, then equilibrium will drive the reaction to produce product having a molecular weight between that of the two streams. It is desirable to reduce the concentration of the desired products in the molecular redistribution zone to as low a concentration as possible to favor the reactions in the desired direction. As such, some routine experimentation may be necessary to find the optimal conditions for conducting the process.

In the event the catalyst deactivates with the time on-stream, specific processes that are well known to those skilled in art are available for the regeneration of the catalysts.

Any number of reactors can be used, such as fixed bed, fluidized bed, ebulated bed, and the like. An example of a suitable reactor is a catalytic distillation reactor which would permit continuous recovery of the desired lower molecular weight product.

Fractional Distillation

The resulting product stream can be distilled to provide a first fraction rich in ethane or a mixture of ethane and propane, a second fraction rich in $C_{3-5}$ paraffins, and a third fraction containing predominantly $C_6$+paraffins. An ethane-rich fraction can also be isolated via known methodology, for example using a deethanizer column as described above. The ethane-rich fraction can be sent to an ethane cracker or an ethane/propane cracker, depending on the quality of the fraction. The $C_{3-5}$ fraction can be recycled through the molecular redistribution stage.

III. Formation of Ethylene or Ethylene/Propylene

The ethane or mixtures of ethane and propane isolated from the product stream are preferably converted to ethylene or mixtures of ethylene and propylene using ethane or ethane/propane crackers. Flexicrackers could be used, although this would not be cost effective. While other methods for converting paraffins to ethylene or mixtures of ethylene and propylene are known, these are not preferred. Suitable EP crackers and conditions for their use are well known to those of skill in the art, and are described in detail below. The products of the EP cracker include ethylene, propylene, and a small amount of heavier material, each of which can be isolated using known methodology.

Ethane and Ethane/Propane Crackers

Ethylene or ethylene/propylene are obtained by steam cracking of ethane and/or propane. Conditions for obtaining ethylene and propylene are well known to those of skill in the art, and are described, for example, in SRI International-Process Economics Program, *Ethylene*, Report 29 E, October 1991, the contents of which are hereby incorporated by reference. Typically, ethane or ethane/propane crackers are used, depending on the feed. With ethane cracking, the amount of propylene produced is relatively small, with a ratio of 48:1 ethylene to propylene. With ethane/propane cracking, the ratio is 8.5:1. However, considering the scale at which ethylene can be produced, the amount of propylene produced may still be commercially significant.

Steam cracking involves subjecting ethane or mixtures of ethane and propane to hydrocarbon cracking or pyrolysis in the presence of steam in tubular reactors in direct-fired heaters (furnaces). Steam does not participate in the pyrolysis reactions directly, but it improves product selectivity and reduces coking in the pyrolysis tubes and downstream quench coolers.

Typically, a number of furnaces operating in parallel are used. The exact number of furnaces depends on the capacity of the furnaces and the desired output. Each furnace includes a convection zone where waste heat is recovered, and a radiant zone where pyrolysis occurs.

A steam-containing ethane or ethane/propane feedstock is preheated in the convection zone to about 538° C. to 649° C.

(1000° F. to 1200° F.) before it crosses over to the radiant zone. Pyrolysis takes place at a temperature of between 788° C. and 899° C. (1450° F. to 1650° F.), with residence times in the radiant zone of between 0.05 to 0.6 seconds, depending on the feedstock and severity of cracking required. The higher the temperature and longer the residence time, the higher the severity of the cracking. The cracked gas is immediately cooled (quenched) to between 338° C. and 510° C. (640° F. to 959° F.), allowing the cracking to stop and allowing the heat to be recovered, for example by generating high pressure steam in heat exchangers. The resulting cooled stream is then flowed toward a direct water quench tower, further cooling the gas with recirculating cold water at a temperature of between 35° C. and 40° C. (95° F. to 105° F.).

The cooled gas is compressed, for example centrifugally compressed, to a pressure of between about 415 and 550 psia in a plurality of stages, typically between four and five stages. Between these stages, water and high molecular weight products are separated. The gaseous product is then washed with a caustic solution or an alkylamine solution followed by a caustic solution to remove any acidic gases, such as carbon dioxide. The gas is then dried with a dessicant, optionally including a glycol. The dried gas is then cooled, for example with propylene and ethylene refrigerants, to cryogenic temperatures. The product is then separated downstream by fractionation. The product separation is typically performed in one of three ways ¾ front-end demethanization, front-end depropanization, or front-end deethanization.

Front-End Demethanization

Front-end demethanization first involves separating tail gases such as carbon monoxide, hydrogen and methane from the $C_2$+components. This involves demethanization at about 425–450 psia, followed by deethanization, hydrogenation of any acetylene that may be present, $C_2$ splitting, depropanization, hydrogenation of any methylacetylene or propadiene that may be present, $C_3$ splitting, and debutanization. A schematic illustration of these processes is shown in FIG. 1.

As shown in FIG. 1, 10 is a holding tank for the ethylene/propylene feed and recycle. The ethylene/propylene feed is transferred to a water wash (20). The washed gas is compressed (30) and subjected to a caustic wash (40). The washed gas is compressed (50), dried (60), and pre-chilled (70). The pre-chilled gas is sent to a demethanizer (80), and the fraction containing methane, tail gas, and hydrogen is sent to a cold box (90) for fractionation into methane, tail gas and hydrogen. The $C_2$+fraction is sent to a deethanizer (100), and the $C_2$ fraction is sent to an acetylene reactor (110) to hydrogenate the acetylene without hydrogenating the ethylene. The effluent from the acetylene reactor is sent to a fractional distillation tower (120) to separate the ethane from the ethylene. The $C_3$+fraction from the deethanizer is sent to a fractional distillation tower (130) to separate the $C_4$+fraction from the $C_3$ fraction. The $C_3$ fraction is sent to a methyl acetylene/propadiene reactor (140) to hydrogenate the methyl acetylene/propadiene without hydrogenating the propylene. The effluent from the methyl acetylene/propadiene reactor is sent to a fractional distillation tower (150) to separate the propane from the propylene.

Front-End Depropanization

In front-end depropanization, acid gases are typically removed after the third compression stage, and $C_3$ and lighter products are separated from $C_4$ and heavier products by depropanization. The $C_{4-5}$ products are preferably recycled in the molecular redistribution reaction, and $C_6$+products used in a reforming process, for example the AROMAX™ process or conventional platforming or rheniforming processes, to form aromatic compounds. Conventional rheniforming processes are well known to those of skill in the art, and are described, for example, in U.S. Pat. No. 3,415,737.

The $C_6$+products can also be isomerized to form components useful in fuel compositions. The $C_3$ and lighter products are compressed in a fourth stage to about 530 psia, and any acetylene present in the stream is catalytically hydrogenated to ethane and ethylene using the hydrogen still present in the stream. The stream is then demethanized and deethanized. The $C_2$ products are then split, the methyl acetylene and propadiene hydrogenated, and the C3 products split.

Figure 2:
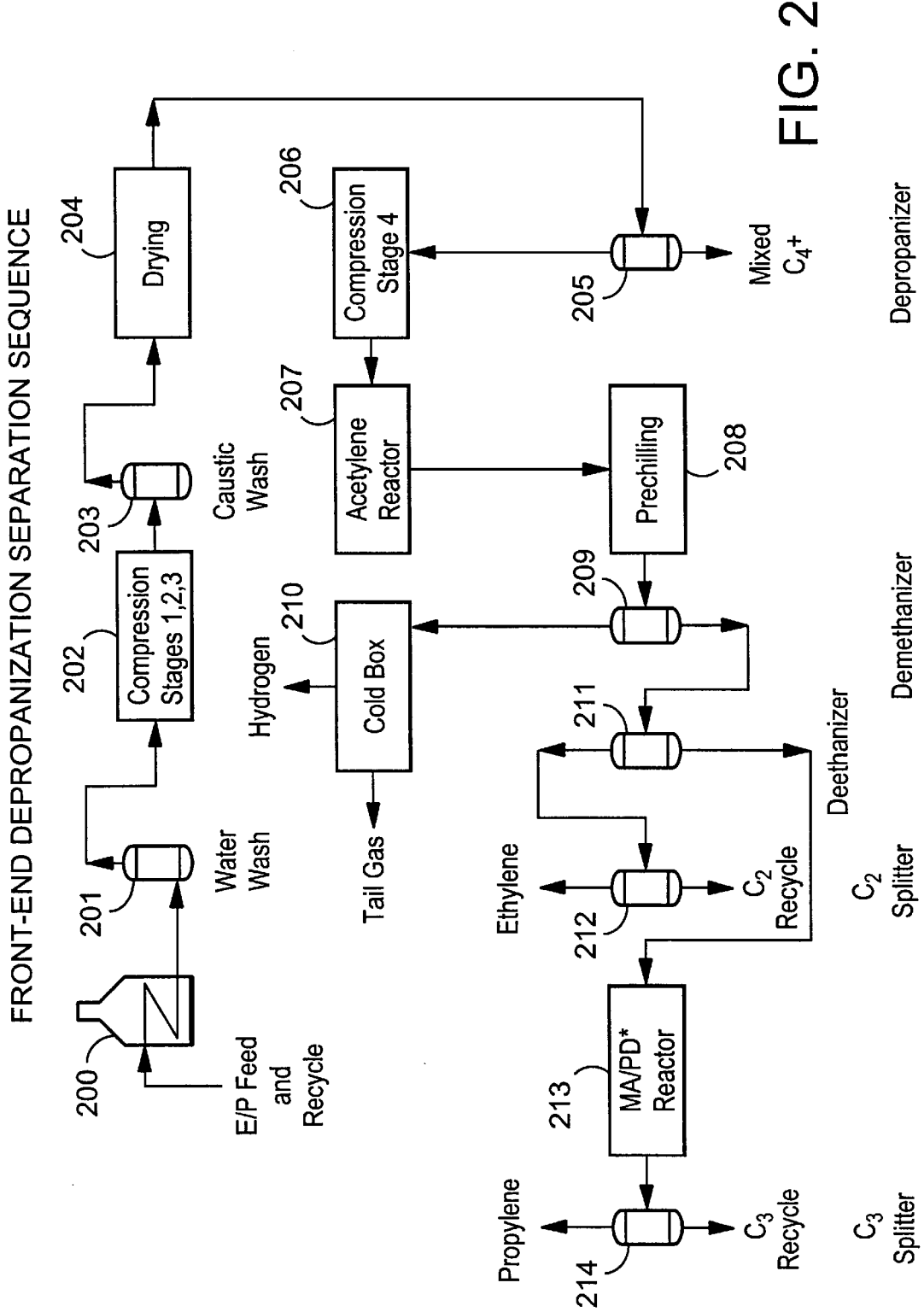
FIG. 2 is a schematic flow diagram representing a front-end depropanization process.

As shown in FIG. 2, 200 is a holding tank for the ethylene/propylene feed and recycle. The ethylene/propylene feed is transferred to a water wash (201). The washed gas is compressed (202) and subjected to a caustic wash (203). The washed gas is dried (204) and sent to a fractional distillation tower (205) to remove $C_4$+products. The $C_3$–fraction is then compressed (206) and acetylene is hydrogenated in an acetylene reactor (207). The stream is pre-chilled (208), and the pre-chilled gas is sent to a demethanizer (209). The tail gas fraction is sent to a cold box (210) to remove hydrogen. The $C_2$+fraction is sent to a deethanizer (211), and the $C_2$ fraction is sent to a fractional distillation tower (212) to separate the ethane from the ethylene. The $C_3$ fraction from the deethanizer is sent to a methyl acetylene/propadiene reactor (213) to hydrogenate the methyl acetylene/propadiene without hydrogenating the propylene. The effluent from the methyl acetylene/propadiene reactor is sent to a fractional distillation tower (214) to separate the propane from the propylene.

Front-End Deethanization

Two methods are generally available for performing front-end deethanization. In one version, known as the Linde AG version, the method is virtually identical to front-end demethanization up to the third compression stage, except that between compression stages, water injection is used to cool the cracked gas directly. The cracked gas is pre-dried with a glycol between the fourth and fifth compression stages and again with a dessicant after the fifth and final stage of compression. The resulting dried gas is deethanized at about 415 psia to separate $C_2$– products from $C_3$+products. Any acetylene in the $C_2$– product stream is catalytically hydrogenated to ethylene and/or ethane. The product stream is then cooled and demethanized at low pressure (e.g., about 140 psia) to remove tail gases. The $C_2$ stream is then split into ethylene and ethane. At the same time, the $C_3$+products are further separated.

In the second version, known as the C. F. Braun version, the cracked gas is washed with caustic after three compression stages, compressed in a fourth stage and dried with molecular sieves. The gas is then pre-chilled, for example using external refrigeration and recycled cold streams, and then deethanized at about 250 psia. A $C_2$– stream is then compressed further to about 540 psia and catalytically hydrogenated to remove acetylene. Then, the stream is demethanized and the $C_2$ products are split into ethane and ethylene. The $C_3$+products are further separated.

Figure 3:
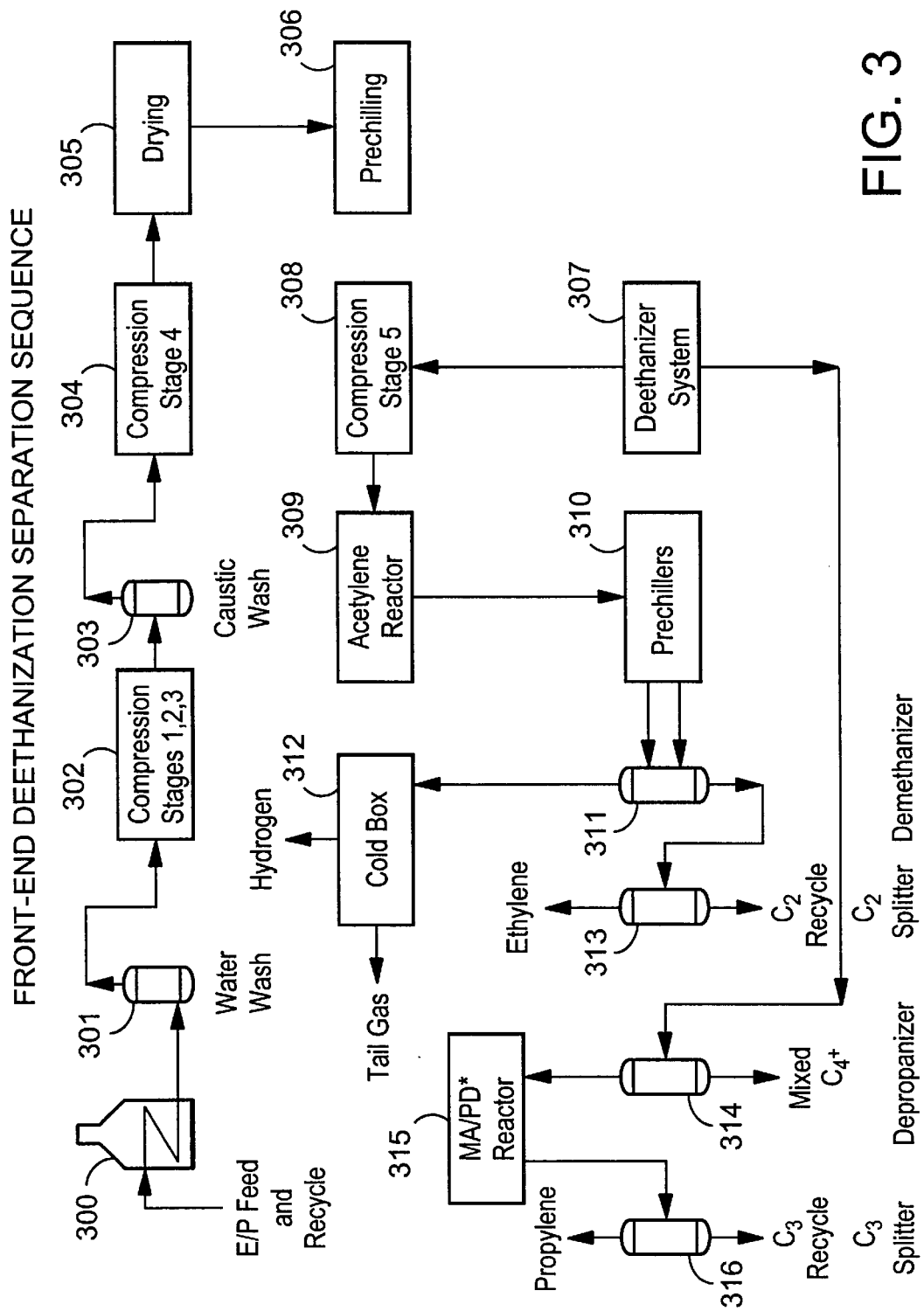
FIG. 3 is a schematic flow diagram representing a front-end deethanization process.

The C. F. Braun version is shown in FIG. 3. Box 300 represents a holding tank for the ethylene/propylene feed and recycle. The ethylene/propylene feed is transferred to a water wash (301). The washed gas is compressed (302) and subjected to a caustic wash (303). The washed gas is compressed (304), dried (305), and pre-chilled (306). The pre-chilled gas is sent to a deethanizer (307), and the C$_2$-fraction is compressed (308) and the acetylene is hydrogenated in an acetylene reactor (309). The fraction is then pre-chilled (310) and sent to a demethanizer (311). The tail gas fraction is sent to a cold box (312) to remove hydrogen. The C$_2$ fraction is sent to a fractional distillation tower (313) to separate the ethane from the ethylene.

The C$_3$+fraction from the deethanizer is sent to a depropanizer (314) and the C$_4$+products are removed. The C$_3$ fraction is sent to a methyl acetylene/propadiene reactor (315) to hydrogenate the methyl acetylene/propadiene without hydrogenating the propylene. The effluent from the methyl acetylene/propadiene reactor is sent to a fractional distillation tower (316) to separate the propane from the propylene.

Additional methods for separating and recovering ethylene involve non-distillative and non-cryogenic techniques, particularly in separating olefins from nonolefins. Chemical absorption and desorption, for example using aqueous silver nitrate solutions, operate at ranges between about 600 psia/ 70° F. and 2 psia/400° F. for absorption and desorption, respectively. Membrane separators, for example those described in U.S. Pat. No. 5,082,481 to Barchas et al., remove approximately 20% of the hydrogen from a pressurized mixed olefin bearing charge gas before refrigerating the charge gas.

These techniques can be combined with other devices, such as flash and distillation equipment (see, for example, U.S. Pat. No. 5,452,581 to Dinh et al.) to provide improved results. For example, membranes can be used to remove hydrogen in the chill train, thus saving energy by moving refrigeration load from the substantially dedicated low temperature refrigeration system to a high temperature refrigeration system. However, they cannot entirely eliminate the chill train, or the low temperature refrigeration system, or the fractional or absorptive distillation. They are preferably used on relatively low volume secondary ethylene containing streams, such as process purges that are high in ethylene content.

Ethylene or Propylene-rich Product Streams

The product of the ethane or ethane/propane cracker described above is a composition that includes mostly ethylene or mixtures of ethylene and propylene. In a preferred embodiment, the composition is a primary ethylene-rich or propylene-rich product stream as such streams are known in the art. It is suitable for all possible end uses in the subsequent manufacture of ethylene derivatives. Most preferably, the composition falls within the stringent specifications for ethylene or propylene product streams in the area of polyethylene or polypropylene manufacture, which requires ethylene or propylene-rich product streams of high purity.

A typical enriched stream has more than about 95 wt. % ethylene or propylene. The stream includes less than about 2000 molar ppm each of substantially inert components such as methane and ethane and less than about 20 molar ppm each of potentially reactive components such as hydrogen, carbon monoxide, carbon dioxide, propylene (in the ethylene stream) or ethylene (in the propylene stream). The streams generally must have this level of purity because of the nature of the derivative processes that use the ethylene or propylene-rich product streams. These processes each suffer varying degrees of adverse process performance and economic impact depending on the levels of the various non-ethylene/propylene components in the stream.

Many derivative processes may not require the historically high levels of ethylene or propylene purity needed for polyethylene or polypropylene manufacture. Ethylbenzene synthesis (see, for example, U.S. Pat. No. 5,476,978 to Smith et al.) can tolerate feeds that include ethylene in concentrations as low as 5 wt. %. Processes which manufacture aldehydes, alcohols, or esters (see, for example, European Patent Application serial number PCT/EP96/00361 by Kiss et al.), can use an ethylene-rich product stream with between 30 and 75 wt. % ethylene, and which can contain appreciable quantities of hydrogen and carbon monoxide. In a less preferred embodiment, the ethylene product stream produced by the processes described herein is rich enough in ethylene for use in these derivative processes.

Fractional Distillation of the C,+Fraction from the Molecular Redistribution Reaction The C,+fraction from the molecular redistribution reaction can be distilled to provide a fraction including mostly C$_{3-5}$ paraffins and a fraction including predominantly C,+paraffins, preferably C$_6$+paraffins. The C$_{3-5}$ fraction can be recycled through the molecular redistribution stage to form additional ethane and C$_6$+paraffins. The process can be repeated in a series of recycles to convert virtually all of the C$_{3-5}$ paraffins to ethane and C$_6$+paraffins.

Isomerization of the Resulting C$_6$ Paraffins

The resulting C$_6$+paraffins can be used to form a variety of products. For example, the C$_6$+product stream can also be used as solvent. Alternatively, the C$_6$+product stream (which can optionally also include C$_5$ products) can be isomerized, particularly for use in gasoline compositions. When the C$_6$+fraction resulting from the molecular redistribution stage is isomerized, the product has more branched paraffins, thus improving its octane value. This can be particularly preferred when preparing fuel compositions where a high octane is desired.

Isomerization processes are typically carried out at a temperature between 200° F. and 700° F., preferably 300° F. to 550° F., with a liquid hourly space velocity between 0.1 and 2, preferably between 0.25 and 0.50. Hydrogen is employed such that the mole ratio of hydrogen to hydrocarbon is between 1:1 and 5:1. Catalysts useful for isomerization processes are generally bifunctional catalysts that include a dehydrogenation/ hydrogenation component (preferably selected from the Group VIII metals of the Periodic Table of the Elements, and more preferably selected from the group consisting of nickel, platinum, palladium and mixtures thereof) and an acid component. Examples of an acid component useful in the preferred isomerization. catalyst include a crystalline zeolite, a halogenated alumina component, or a silica-alumina component. Such paraffin isomerization catalysts are well known in the art.

Other Processes for Altering the C,+Product Stream

In a preferred embodiment, at least a portion of the C$_6$+product stream is reformed, for example using reforming conditions, to form aromatic products. Reforming is a complex process and involves a number of competing processes or reaction sequences. These include dehydrogenation of cyclohexanes to aromatics, dehydroisomerization of alkylcyclopentanes to aromatics, and dehydrocyclization of acyclic hydrocarbons to aromatics. The hydrocracking of paraffins to light products boiling outside the gasoline range and the dealkylation of alkylbenzenes are undesirable reactions in reforming processes. As the C$_6$+product stream includes predominantly acyclic paraffins, the major reforming reaction is dehydrocyclization.

Conditions suitable for reforming C$_6$+product streams are well known in the art. Representative reforming processes include the AROMAX™ process and platforming or rheniforming processes. The AROMAX™ process is well known to those of skill in the art, and is described, for example, in *Petroleum & Petrochemical International*, Volume 12, No. 12, pages 65 to 68.

These processes, their commercial startup conditions and their useful range of process operating conditions are all well known to those skilled in the art. These processes can be carried out in a single reactor or in a series of reactors.

Feedstock

The feedstock for the reforming reaction is a normal $C_6$+paraffinic fraction, preferably a normal $C_{6-8}$ paraffinic fraction, with a minimum of isoparaffins. More preferably, the stream includes predominantly $C_6$ and $C_7$ hydrocarbons. Using the AROMAX™ process, yields of aromatic compounds are nearly 90% when this stream is used. Isoparaffins such as 2,2-dimethylbutane or 2,3-dimethylbutane are preferably not used, as they do not reform well in AROMAX™ or other reforming conditions.

As with the molecular redistribution reaction described above, the feed should also be substantially free of sulfur, nitrogen, metals and other known poisons. Methods for removing such poisons from the feed have been discussed above. In a preferred embodiment, the $C_6$+hydrocarbons contacting the catalyst are substantially dry and free of sulfur, i.e., sulfur levels are preferably maintained below about 50 ppb, preferably below about 25 ppb and more preferably below about 10 ppb. Sulfur removal systems are well known in the ultra-low sulfur reforming art. If the product of the molecular redistribution reaction in the $C_6$+range is combined with other feedstocks in that range, sulfur and other impurities need to be removed.

Conversion Processes

The catalytic reforming process is a low sulfur reforming process, preferably using a bound, halided Pt L-zeolite catalyst. Catalytic reforming is well known. For example, techniques such as platforming and rheniforming are described in the book *Catalytic Reforming* by D. M. Little, PennWell Books (1985), which is incorporated herein by reference in its entirety.

The reaction is preferably conducted at a temperature between 400 and I 100° F., more preferably between 800 and 1050° F. In the temperature range of from 400 to 600° C., the reforming reaction can occur with acceptable speed and selectivity. When using traditional reforming catalysts, if the operating temperature is below 400° C., the reaction speed is insufficient and consequently the yield is too low for industrial purposes. When the operating temperature is above 600° C., interfering secondary reactions such as hydrocracking and coking may occur, reducing the yield. These secondary reactions are minimized using the bound, halided, zeolite catalysts described herein. The AROMAX™ Process is preferred when $C_{6-7}$ feedstocks are used, as it provides nearly 905 yields of benzene using this feedstock. Conventional platforming and rheniforming processes can be preferred when C7+feeds are used, as they give high yields of aromatics.

The pressure is preferably between 0 and 400 psig, more preferably between 15 and 150 psig. The recycle hydrogen rate is sufficient to yield a hydrogen to hydrocarbon mole ratio for the feed to the reforming reaction zone between 0.1 and 20, more preferably between 0.5 and 10 and most preferably between 2 and 6. The liquid hourly space velocity (LHSV) for the hydrocarbon feed over the reforming catalyst is between 0.1 and 10 hr$^{-1}$, more preferably between 0.5 and 5 hr$^{-1}$. Reforming produces hydrogen. Thus, additional hydrogen is not needed except when the catalyst is reduced upon startup, and when the feed is first introduced. Once reforming is underway, part of the hydrogen that is produced is preferably recycled over the catalyst.

In one embodiment, aromatics are prepared by first preparing a halided zeolite catalyst, bringing the catalyst on stream using commercial startup conditions, and contacting the catalyst with the $C_6$+paraffinic fraction at catalytic reforming conditions to produce aromatics. The catalyst is preferably prepared by washing a calcined, bound zeolite catalyst base with an aqueous liquid, and adding at least one halogen-containing compound and a Group VIII metal compound to the washed base.

In a preferred embodiment, the $C_6$+fraction is converted to an aromatic product stream by catalytic conversion of the $C_6$+feed under conversion conditions that include a commercial-type catalyst startup (at a low gas flow rate and a slow heat-up rate). The process preferably uses a bound and washed halided zeolite catalyst containing a Group VIII metal, where the halided catalyst has a cycle length of >1200 hr following startup. The halided catalyst is preferably prepared by a process that involves washing a bound zeolite catalyst base or catalyst before halide addition and before reduction.

The feed can be contacted with the catalyst in a fixed bed system, a moving bed system, a fluidized system, or a batch system. Either a fixed bed system or a moving bed system is preferred. In a fixed bed system, the preheated feed is passed into at least one reactor that contains a fixed bed of the catalyst. The flow of the feed can be upward, downward or radial. The effluent from the catalytic reforming reaction zone can be separated into the desired streams or fractions.

Catalyst Selection

The reforming catalysts used in the AROMAX™ process or similar reforming processes are preferably bound and include a Group VIII metal, preferably Pt. The catalysts are also preferably halided and, more preferably, are (water) washed, bound, halided catalysts. The term "catalyst" includes both the final catalyst as well as precursors of the final catalyst. Precursors of the final catalyst include, for example, the calcined form of the catalyst containing the catalytic metal and also the catalyst prior to activation by reduction. As used herein, the term "bound" is intended to describe a zeolite, binder combination that is fori-ned into aggregates such as pellets, pills, extrudates and the like. The term "catalyst base", as used herein, refers to a bound zeolite.

Zeolites

Catalysts useful in the reforming reaction typically include one or more zeolites or non-zeolitic molecular sieves and at least one catalytic metal, preferably a Group VIII metal. The catalysts typically also include a binder such as a refractory oxide, e.g., silica, alumina, chlorided alumina or silica-alumina. Preferred zeolites and/or molecular sieves are selected from those of the large and intermediate pore variety. The AROMAX™ process traditionally uses PtBaK/L-zeolite as a catalyst. Traditional platforming and rheniforming processes use $Pt/Al_2O_3$ or $PtRe/Al_2O_3$ as the catalyst. These and other catalysts and suitable reforming conditions are described, for example, in U.S. Pat Nos. 3,546,102; 3,574,092; 3,679,575; 4,018,711; 4,104,320; 4,347,394; 4,370,224, 4,417,083; 4,434,311; 4,447,316 and 5,559,068.

Catalysts including platinum on chlorinated-alumina supports and Pt-X on alumina or chlorinated-alumina supports, where X is rhenium, iridium or tin have been used in catalytic reforming reactions. U.S. Pat. No. 4,370,224 discloses a multi-metallic reforming catalyst that includes platinum, iridium, copper, selenium and halogen, composited with an inorganic oxide support or carrier, preferably alumina. Zeolite containing reforming catalysts, for example the zeolite mordenite, ZSM-type zeolites, zeolite L, Faujasites X and Y, and the zeolite omega have been used.

Representative of the large pore zeolites are ZSM-3, ZSM-4, ZSM-10, ZSM-12, ZSM-20, zeolite beta, zeolite omega, zeolite L, zeolite X, zeolite Y, REY, USY, RE-USY, mordenite, LZ-210, LZ-210-M, LZ-210-T, LZ-210-A, SSZ-24, SSZ-26, SSZ-31, SSZ-33, SSZ-35, SSZ-37, SSZ-41, SSZ-42, SSZ-44 and MCM-58. ZSM-3 is described in U.S. Pat. No. 3,415,736. ZSM-4 is described in UK Application No. 1, 117,568. ZSM-10 is described in U.S. Pat. No. 3,692,470. ZSM-12 is described in U.S. Pat. No. Pat. 3,832,449; ZSM-20 is described in U.S. Pat. No. 3,972,983. Zeolite beta is described in U.S. Pat. No. Re. 28,341 (of original U.S. Pat. No. 3,308,069). Zeolite omega is described in U.S. Pat. No. 4,241,036. Zeolite L is described in U.S. Pat. No. 3,216,789. Zeolite X is described in U.S. Pat. No. 2,882,244. Zeolite Y is described in U. S. Pat. No. 3,13 0,007. LZ-2 10, LZ-2 I OM, LZ-2 I 0-T, LZ-2 I O-A and mixtures thereof are described in U.S. Pat. No. 4,534,853. SSZ-24 is described in U.S. Pat. No. 4,834,977. SSZ-26 is described in U.S. Pat. No. 4,910,006. SSZ-31 is described in U.S. Pat. No. 5,106,801. SSZ-33 is described in U.S. Pat. No. 4,963,337. SSZ-35 is described in U.S. Pat. No. 5,316, 753. SSZ-37 is described in U.S. Pat. No. 5,254,514. SSZ-41 is described in U.S. Pat. No. 5,591,421. SSZ-42 is described in U.S. Ser. No. 08/199,040. SSZ-44 is described in U.S. Pat. No. 5,580,540. MCM-58 is described in U.S. Pat. No. 5,437,855. The entire contents of all these patents and patent applications are incorporated herein by reference.

Preferably, the catalyst is an L-zeolite or a zeolite having an L-zeolite-type channel structure and size, such as ECR-2, which is described in U.S. Pat. No. 4,552,731, and ECR-31, which is described in U.S. Pat. No. 5,624,657 (Vaughan). Preferably the catalyst is a monofunctional, non-acidic K L-zeolite. Acidity in the L-zeolite generally leads to poor performance in catalytic reforming. Examples of useful L-zeolites include those described in U.S. Pat. No. 3,216, 789 (Breck), U.S. Pat. No. 4,552,731 (Vaughan), U.S. Pat. No. 4,544,539 (Wortel), U.S. Pat. No. 5,491,119 (Verduijn) and U.S. Pat. No. 4,530,824 (assigned to Tosoh Ltd.). The entire contents of all these patents are incorporated herein by reference. One useful non-acidic L-zeolite is manufactured by Union Oil Product (UOP), Mobile, Ala. A preferred non-acidic L-zeolite is manufactured by Tosoh Ltd., Japan, and sold under the name HSZ-500KOA. For these non-acidic zeolites, potassium is a preferred cation; a preferred catalyst comprises K L-zeolite.

Preferred catalysts are monofunctional. They do not have the acid function of conventional reforming catalysts. In contrast, conventional reforming catalysts are bifunctional, with an acid and a metal function. An example of such a catalyst is PtRe/Al$_2$O$_3$. Examples of monofunctional catalysts include platinum on L-zeolite, wherein the L-zeolite has been exchanged with an alkali metal, as disclosed in U.S. Pat. No. 4,104,320 to Bernard et al.; platinum on L-zeolite, wherein the L-zeolite has been exchanged with an alkaline earth metal, as disclosed in U.S. Pat. No. 4,634,518 to Buss and Hughes; and platinum on L-zeolite as disclosed in U.S. Pat. No. 4,456,527 to Buss, Field and Robinson. The entire contents of all these patents are incorporated herein by reference.

The term "non-acidic" is understood by those skilled in this area of art, particularly by the contrast between mono-functional (non-acidic) reforming catalysts and bifunctional (acidic) reforming catalysts. One method of achieving non-acidity is by replacing protons with alkali and/or alkaline earth metals in the zeolite. This is preferably achieved, along with other catalyst enhancements, by an ion exchange process on the synthesized zeolite.

The composition of type L zeolite expressed in terms of mole ratios of oxides, may be represented by the following formula:

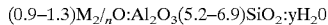

$$(0.9-1.3)M_2/_nO:Al_2O_3(5.2-6.9)SiO_2:yH_2O$$

In the above formula M represents a cation, n represents the valence of M, and y may be any value from 0 to about 9. Zeolite L, its X-ray diffraction pattern, its properties, and method for its preparation are described in detail in, for example, U.S. Pat. No. 3,216,789, the contents of which is hereby incorporated by reference. The actual formula may vary without changing the crystalline structure. For example, the mole ratio of silicon to aluminum (Si/Al) may vary from 1.0 to 3.5.

As discussed above, one preferred embodiment of the invention uses monofunctional Pt L-zeolite catalysts that have been treated with halogen-containing compounds. This type of halogen treatment is known. For example, U.S. Pat. No. 5,091,351 to Murakawa et al., discloses preparing a Pt L-zeolite catalyst, and then treating it with a halogen-containing compound. Other related patents that disclose halided L-zeolite catalysts include EP 498,182A or U.S. Pat. No. 5,354,933, which discloses co-impregnation of an L-zeolite with NH$_4$Cl and NH$_4$F; U.S. Pat. Nos. 4,681,865, 4,761,512 and 5,073,652 to Katsuno et al. These patents are all incorporated herein by reference. One preferred hiz-cat (also referred to herein as "halided catalyst" or "halided zeolite catalyst") for catalytic reforming comprises halided platinum K L-zeolite catalyst, especially one containing both chloride and fluoride.

Examples of useful intermediate pore size zeolites include ZSM-5, ZSM- 11, ZSM-22, ZSM-23 (an unusual zeolite with 7 and 9 ring channels rather than the typical 10 ring channels found in conventional intermediate pore size zeolites), ZSM-35; ZSM-48, ZSM-57, SUZ-4, SSZ-23; SSZ-25; and SSZ-32. ZSM-5 is described in U.S. Pat. No. Re. 29,948 (of original U.S. Pat. No. 3,702,886). ZSM-11 is described in U.S. Pat. No. 3,709,979. ZSM-22 is described in U.S. Pat. No. 4,556,477. ZSM-23 is described in U.S. Pat. No. 4,076,842. ZSM-35 is described in U.S. Pat. No. 4,016, 245. ZSM48 is described in U.S. Pat. No. 4,585,747. SUZ-4 is described in EP Application No. 353,915. SSZ-23 is described in U.S. Pat. No. 4,859,422. SSZ-25 is described in U.S. Pat. Nos. 4,827,667 and 5,202,014. SSZ-28, a small pore size zeolite which can also be used, is described in U.S. Pat. No. 5,200,377. SSZ-32 is described in U.S. Pat. No. 5,053,373. SSZ-36, another small pore size zeolite which can also be used, is described in U.S. Ser. No. 60/034,252. The entire contents of all these patents and patent applications. are incorporated herein by reference.

In addition to silicon, the useful zeolites herein can contain one or more framework elements other than, or in addition to, aluminum, e.g., the borosilicate zeolites. Also, the zeolites can be modified to alter their as-synthesized framework silica to alumina ratio.

Suitable catalysts can also include non-zeolitic molecular sieves with intermediate or large size pores. Non-zeolitic molecular sieves are microporous compositions that are formed from [AlO$_2$] and [PO$_2$] tetrahedra and have electrovalently neutral frameworks. See U.S. Pat. No. 4,861,743.

Non-zeolitic molecular sieves include aluminophosphates (AlPO$_4$) as described for example in U.S. Pat. No. 4,310, 440, metalloalummophosphates, as described in U.S. Pat.

Nos. 4,500,651; 4,567,029; 4,544,143; and 4,686,093 and nonmetal substituted aluminophosphates as described in U.S. Pat. No. 4,973,785, and microporous, crystalline metallophosphates such as those described in U.S. Pat. No. 4,440,871.

Useful catalysts also include intermediate pore silicoaluminophosphates (SAPO's) as the non-zeolitic molecular sieve component. Intermediate pore SAPO's include SAPO-11, SAPO-31, SAPO-41 and SM-3. U.S. Pat. No. 4,440,871 describes SAPO's generally and SAPO-11, SAPO-31, and SAPO41 specifically. The preparation of SM-3 and its unique characteristics are described in U.S. Pat. No. 5,158,665. All these patents are incorporated herein by reference.

Binders

The zeolites and/or molecular sieves are bound. They are preferably composited with matrix materials resistant to the temperatures and other conditions employed in hydrocarbon conversion processes. Such matrix materials can include active and inactive materials. Frequently, binders such as naturally occurring clays and inorganic oxides are added to improve the crush strength of the catalyst. The selection of binders and binding conditions depends on the zeolite and its intended use.

Suitable binder materials include synthetic or naturally occurring zeolites, alumina, clays such as montmorillonite and kaolin, and the refractory oxides of metals of Groups IVA and IVB of the Periodic Table of the Elements. Particularly useful are the oxides of silicon, alumina (although alumina is less preferred for the AROMAX™ Process), titanium and zirconium, with silica being preferred, especially low acidity silica Combinations of such oxides with other oxides are also useful, for example silica-alumina, silica-magnesia, silica-zirconia, silica-thoria, silica-beryllia, silica-titania, titania-zirconia, silica-alumina-thoria, silica-alumina-zirconia, silica-alumina-magnesia and silica-magnesia-zirconia. These oxides can be crystalline or amorphous, or can be in the form of gelatinous precipitates, colloids, sols, or gels. Silica in the form of a silica sol is a preferred binder. A preferred silica sol has about 30 wt % silica and contains small particles (7–9 nm in diameter), which result in catalysts with good attrition resistance and excellent crush strengths.

Extrusion aids and viscosity modifiers are generally used in addition to the binders for forming pellets or extrudates from zeolites and/or molecular sieves. These additives are typically organic compounds such as cellulose based materials, for example Methocel' sold by Dow Chemical Co., ethylene glycol, and stearic acid. Many such compounds are known in the art. These additives should not leave a detrimental residue, i.e., one with undesirable reactivity or one that can block pores, after calcination. Preferably, the residues do not add significant amounts of alkali or alkaline earth ash to the catalyst. The above-described washing will remove low levels of these materials. The residue from the extrusion aid is preferably less than a few tenths of a percent by weight, more preferably less than 0.1 wt %.

Methods for preparing catalyst compositions are well known to those skilled in the art and include such conventional techniques as spray drying, pelletizing, extrusion, various sphere-making techniques and the like. The methods of in-extrudate formation of the zeolite/binder described in U.S. Pat. No. 5,558,851 to Miller and in U.S. Pat. No. 5,514,362 can also be used. The entire contents of these patents are incorporated herein by reference.

The relative proportions of zeolite to the binder/matrix can vary widely. Generally the zeolite content ranges from between about 1 to about 99 wt %, and more usually in the range of from about 5 to about 95 wt %, of the dry composite, more typically 50–85 wt %.

Preferably, whole extrudates rather than crushed extrudates or unbound zeolites are used. Bound zeolites reduce the pressure drop through a reactor, provide improved flow rates, and are easier to load and unload. However, the diffusion characteristics of whole extrudates are quite different from those of unbound powdered zeolites. The interaction of a diffusing gas, such as a halocarbon, is different for a powdered versus a bound zeolite. Diffusion differences would also be especially significant if the catalyst evolves materials such as gases or solids, for example during startup. Moreover, the act of binding itself—including selecting binding materials and the binding method—as well as calcining, can affect catalyst performance. For example, the binder can interact with the sieve by simply blocking internal and external sites or by chemical interaction (e.g., alkali from a basic sieve like the preferred L-zeolite of the present invention and silica are known to react under thermal and hydrothermal calcination conditions). Moreover, the distribution of impregnated materials may vary considerably on zeolite powder versus bound zeolites. Thus, studies on powders alone cannot be used to predict commercial performance of bound zeolite catalysts.

Group VIIIB Metal

The catalyst preferably includes at least one Group VIIIB metal, preferably a noble metal (Pt, Pd, Rh, Ir, Ru, Os), and more preferably, platinum. Other metal promoters, such as tin, germanium, cobalt, nickel, and combinations thereof can also be used. Preferred amounts of metal are 0.1 to 5 wt %, more preferably 0.1 to 3 wt %, and most preferably 0.3 to 1.5 wt %, based on the L-zeolite. Platinum compounds that form positively charged platinum complex ions in solution are the preferred source of platinum. Platinum tetraammine chloride and nitrate are especially preferred.

Additionally, one or more non-platinum group metals such as tin, indium and Group VIIB metals such as rhenium can be added. Examples include Pt/Sn, Pt/Pd, Pt/Ni, and Pt/Re. These metals can be readily introduced into the composite employing a variety of known and conventional techniques, e.g., ion-exchange, incipient wetness, pore fill, impregnation, etc. Care should be taken so that the Group VIIIB metal, e.g., platinum, is incorporated in a manner that results in excellent and uniform dispersion. The incipient wetness impregnation method is preferred.

Halides

The catalysts are preferably hiz-cats. The term "hiz-cat" is intended to include zeolite catalysts that result from adding halogen-containing compounds to or from halide impregnation of zeolites, catalyst bases (i.e., bound zeolites) or zeolite catalysts (i.e., zeolites containing catalytic metal). The halides of the hiz-cats are in addition to those that may be incorporated into the catalyst from the catalytic metal source; that is, this halogen addition or impregnation is not just that associated with conventional platinum loading and impregnation, where platinum halides are often used. Nor does this halogen treatment include conventional zeolite ion exchange operations. Zeolite ion exchange sometimes uses a halide salt, such as KCl, to replace the cations in the zeolite; this ion exchange can leave small amounts of halide on the catalyst. Moreover, the term hiz-cat is not intended to include catalysts where halide is added using alkali halides (e.g., KCl) or alkaline earth halides. Added alkali is believed to be detrimental to hiz-cats performance.

The form in which the halide is present in hiz-cats is unknown, and may be as ionic halide, neutral halide, or it may be part of a compound such as a silica halide or Pt halide. The term "halide" is used in a broad sense, and is not intended to denote the ionic state of the added halogen or of the halogen associated with the catalyst.

The halide can be chloride, fluoride, bromide, iodide, or combinations thereof. Preferably, the hiz-cat contains chloride and/or fluoride, more preferably both. Especially preferred hiz-cats can be prepared by treating the bound zeolite or bound catalyst with halocarbons such as freons or with other chlorine-containing and/or fluorine-containing compounds, e.g. by impregnation with ammonium chloride and ammonium fluoride. Preferred hiz-cats useful in this invention have high total halide after calcination (this includes all halides, e.g. both chloride and fluoride), i.e., they contain at least about 0.9 wt % halide, preferably at least about 1.1 wt % and more preferably at least about 1.3 wt % total combined halide. More than about 5 wt % halide does not appear to provide significant advantages. When chloride and fluoride are both present, the weight ratio of CI to F can vary. Preferably it is between 1:10 and 10:1. More preferably chloride and fluoride are added in a weight ratio of about 1:1.

The terms "chloride retensivity" and "retained chloride" denote the residual chloride content of the catalyst after dry-out, reduction and about 300 hr on-stream. Hizcats evolve chloride during these steps, especially during reduction. Thereafter, the chloride level on the catalyst remains substantially constant as the catalyst is brought onstream and operated. After startup, some halide does continue to evolve, but very slowly. Care should be taken not to overheat the catalyst, (i.e., temperatures above about 950° F.) since additional chloride will evolve, and this overheating is not desirable.

Bound hiz-cat performance can be significantly improved by washing, for example, with water, before the halide is added. Preferred catalysts retain less of the added chloride than poor catalysts, even though the retained chloride, i.e. the "chloride retensivity", is independent of startup conditions. The sodium content of preferred catalysts is about 0.4 wt %. Preferred catalysts include less than about 0.5 wt % chloride, more preferably less than about 0.45 wt % and most preferably less than 0.4 wt % chloride.

Hiz-Cat Preparation

Hiz-cats can be prepared by extruding and then washing either the bound catalyst or the catalyst base before halide addition. Preferably, the catalyst is prepared by:
(a) preparing a calcined silica-bound zeolite catalyst base;
(b) washing the bound zeolite catalyst base with an aqueous liquid, and
(c) incorporating a group VIIIB metal and halogen-containing compound(s) comprising chlorine and fluorine into the washed base to produce a halided zeolite catalyst.

Preferably, the catalyst is prepared using a low alkali, e.g., low sodium, extrusion aid in step (a). The Pt and halogen-containing compounds can be incorporated sequentially or, preferably, simultaneously. A calcined catalyst base is preferably washed before adding the halogen-containing compounds and the Group VIIIB metal, e.g., platinum. In this way, these added components are not washed out of the catalyst. The catalyst base is preferably washed with one or more volumes of wash water. The washing desirably removes at least 20%, preferably at least 50%, of the readily removable alkali.

Catalyst performance can also be improved by various ion exchange processes. Cation exchange, such as with potassium and the like, often includes a wash step. Hiz-cat performance is improved when the ion exchange includes a wash step.

Isolation of Aromatic Products

Benzene, toluene and $C_8$ aromatic streams (i.e., xylenes and ethylbenzene) can be recovered using conventional techniques such as distillation and extraction.

Figure 4:
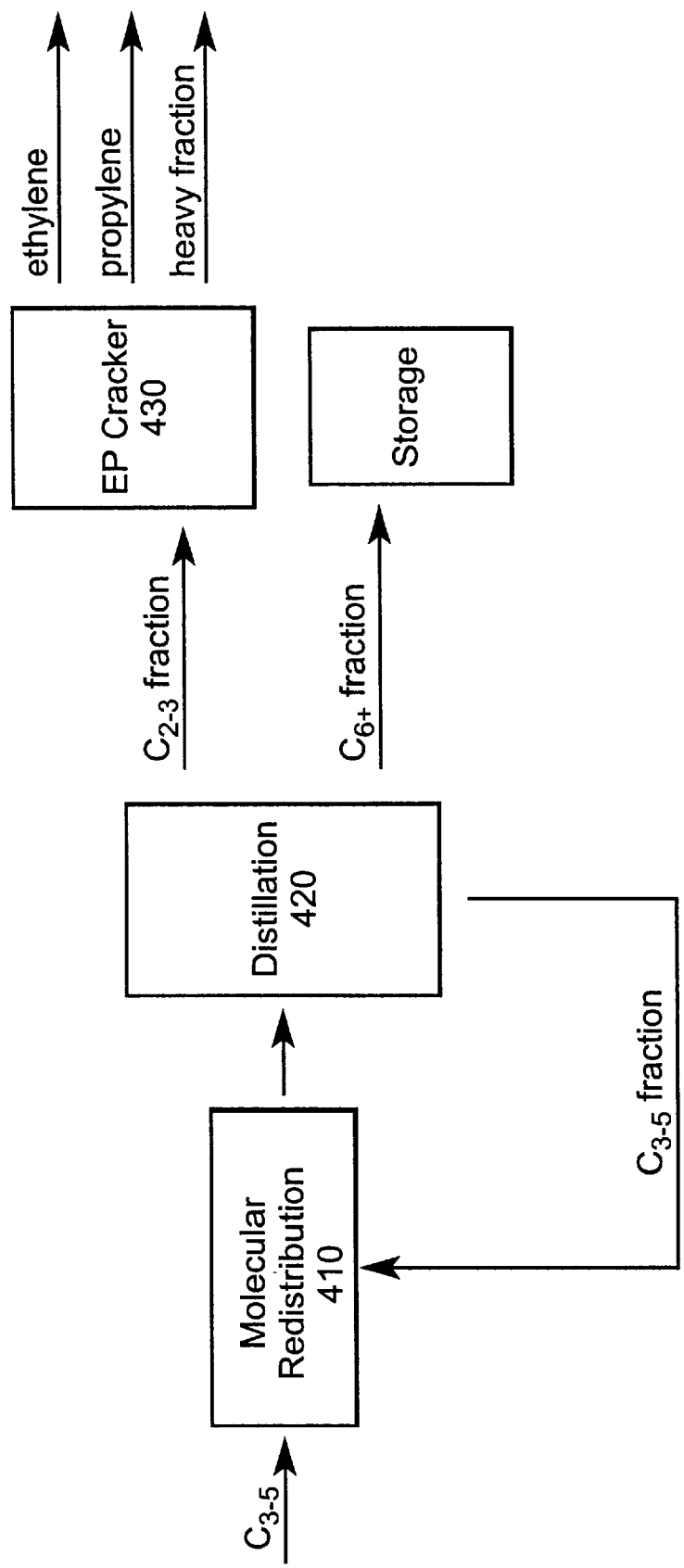
FIG. 4 is a schematic flow diagram representing one embodiment of the invention.

The overall process will be readily understood by referring to the flow diagram in FIG. 4. In the flow scheme contained in FIG. 4, the process is practiced in batch operation. However, it is possible to practice the present invention in continuous operation.

Box 410 is a reactor that dehydrogenates a $C_{3-5}$ paraffin fraction to form olefins, metathesizes the olefins, and rehydrogenates the olefins to form paraffins (molecular redistribution). Following molecular redistribution, the reaction mixture is fractionally distilled (420) to yield a $C_{2-3}$ fraction, a $C_{3-5}$ fraction and a $C_6$+fraction. The is cracked in an EP cracker (430), and the product separated by distillation to yield an ethylene-rich fraction, a propylene-rich fraction and a heavy fraction. The $C_{3-5}$ fraction is sent back to the molecular redistribution stage (410). The $C_6$+fraction is collected separately.

The following examples will help to further illustrate the invention but are not intended to be a limitation on of the scope of the process.

EXAMPLES

Example I

A dehydrogenation/hydrogenation catalyst component was prepared by dissolving 0.6758 grams of $(NH_3)_4Pt(NO_3)_2$ (50.01 wt. % Pt) and 3.3557 grams $LiNO_3$ in 52.8 grams of water. The solution was impregnated overnight in 67.58 grams of alumina spheres obtained from Condea Chemie (1.7 mm, alumina spheres, 24–42 mesh fraction). The impregnated particles were calcined in air initially at a temperature of 250 degrees F., raised to 700 degrees F. over a period of 5 hours, and held for 8 hours at 700 degrees F. The catalyst component was cooled to room temperature within about 5 hours.

Example 2

An olefin metathesis catalyst component was prepared by dissolving 2.3125 grams of ammonium metatungstate (90.6 wt. % $WO_3$) in 36.1 grams of water. The solution was impregnated overnight on 26.4 grams of silica gel manufactured by W. R. Grace/Davison (silica gel grade 59, 24–42 mesh fraction). The resulting impregnated material was calcined in the same manner as the component described in Example 1, above.

Example 3

The molecular redistribution catalyst was prepared by mixing 3.1 cc of the dehydrogenation/hydrogenation component prepared in Example 1 and 0.9 cc of the olefin metathesis component prepared in Example 2. The catalyst mixture (4.0 cc catalyst volume) was loaded into a ¼ inch stainless steel tube reactor which was mounted into an electric furnace containing three heating zones. The catalyst mixture was first dried in nitrogen flow (100 cc/min.) from room temperature to 400 degrees F. within a period of one hour. The mixture was reduced in hydrogen flow (100 cc/min.) using a temperature program consisting of 400 degrees F. to 900 degrees F. within one hour and holding it at 900 degrees F. for 12 hours. Subsequently the catalyst mixture was purged with a nitrogen flow for about one hour and cooled to the reaction temperature (e.g., 800 degrees F.). The reactor was pressurized the reaction pressure (e.g., 1500–2000 psig) with nitrogen. To start the molecular redistribution reaction, the nitrogen was switched to a hydrocarbon feed consisting of either propane, a propane/ 1-butane/n-butane mixture or a propane/ibutane/n-butane/n-pentane mixture which was delivered at a pre-selected feed rate e.g., 2.0 or 4.0 cc/hr).

Example 4

The molecular redistribution reaction of propane was carried out as described in Example 3. The results obtained at 750 degree F., 1500 psig, and 1.0/0.5 LHSV are given in Table 1.

TABLE 1

| LHSV | 1.0 | 0.5 |
|---|---|---|
| Propane Conversion, % | 44.5 | 58.0 |
| Yield, wt. % | | |
| Methane | 0.3 | 0.7 |
| Ethane | 16.9 | 23.6 |
| n-Butane | 18.1 | 19.1 |
| n-Pentane | 5.4 | 7.4 |
| n-Hexane | 1.6 | 2.8 |
| C7 + and unknowns | 2.2 | 4.4 |

Example 5

The molecular redistribution reaction of a mixture of propane, i-butane and n-butane was carried out as described in Example 3. The feed composition and the results obtained under various conditions are given in Table 2.

TABLE 2

| Temperaure, ° 4 F. | — | 750 | 800 | 800 |
|---|---|---|---|---|
| Pressure, psig | — | 2000 | 2000 | 2000 |
| LHSV | — | 0.5 | 0.5 | 0.25 |
| Feed Composition, wt. % | | | | |
| Propane | 61.3 | — | — | — |
| i-Butane | 16.9 | — | — | — |
| n-Butane | 21.8 | — | — | — |
| Propane Conversion, wt. % | — | 38.1 | 40.4 | 48.4 |
| 1-Butane Conversion, wt. % | — | 52.2 | 55.4 | 55.7 |
| n-Butane Conversion, wt. % | — | 25.0 | 28.1 | 32.2 |
| Total C3/iC4/nC4 Conversion, wt. % | — | 37.6 | 40.2 | 46.1 |
| Yield, wt. % | | | | |
| Methane | — | 0.6 | 1.1 | 2.9 |
| Ethane | — | 14.8 | 16.7 | 19.5 |
| 1-Pentane | — | 6.0 | 5.9 | 5.6 |
| n-Pentane | — | 6.0 | 5.8 | 5.7 |
| 2-Methylpentane | — | 2.1 | 2.0 | 2.1 |
| 3-Methylpentane | — | 1.2 | 1.2 | 1.2 |
| n-Hexane | — | 2.1 | 2.1 | 2.1 |
| Other C6 paraffins | — | 0.1 | 0.1 | 0.1 |
| C7+ and unknowns | — | 4.7 | 5.3 | 6.9 |

While the present invention has been described with reference to specific embodiments, this application is intended to cover those various changes and substitutions that may be made by those skilled in the art without departing from the spirit and scope of the appended claims.

What is claimed is:

1. A process for preparing an ethylene-rich product stream, the process comprising;
    (a) contacting a $C_{3-5}$ containing paraffinic feedstock with a catalyst bed which includes a dehydrogenation/hydrogenation catalyst and an olefin metathesis catalyst under conditions which dehydrogenate the paraffins to olefins, metathesize the olefins, and rehydrogenate the olefins, to provide a product stream;
    (b) isolating a first fraction rich in ethane from the product stream; and
    (c) subjecting the first fraction to an ethane cracker and/or an ethane/propane cracker to form an ethylene-rich product.

2. A process for preparing an ethylene-rich product stream, the process comprising;
    (a) contacting a $C_{3-5}$ containing paraffinic feedstock with a catalyst bed which includes a dehydrogenation/hydrogenation catalyst and an olefin metathesis catalyst under conditions which dehydrogenate the paraffins to olefins, methathesize the olefins, and rehydrogenate the olefins, to provide a product stream;
    (b) isolating a first fraction rich in ethane from the product stream;
    (c) isolating a second fraction rich in propane, butane and pentane from the product stream; and
    (d) subjecting the first fraction to an ethane cracker and/or an ethane/propane cracker to form an ethylene-rich product.

3. The process of claim 2, further comprising repeating steps (a) through (c) with the second fraction.

4. The process of claim 1, further comprising isolating a third fraction that includes predominantly $C_6$+paraffins.

5. The process of claim 4, further comprising isomerizing at least a portion of the $C_6$+paraffins.

6. The process of claim 4, further comprising subjecting at least a portion of the $C_6$+paraffins to a catalytic reforming process.

7. The process of claim 6, wherein the reforming process comprises contacting at least a portion of the $C_6$+paraffins with a catalyst comprising a bound Group VIII metal and a molecular sieve at a temperature of 400°–1,100° F., a pressure of O to 400 psig, a hydrogen to hydrocarbon mole ratio of between 0.1 and 20, and an LHSV of 0.1 to 10 hr.

8. The process of claim 6, wherein the reforming process is a platforming or rheniforming process.

9. The process of claim 1, wherein the at least a portion of the $C_{3-5}$ paraffinic feedstock is obtained via demethanization and deethanization of natural gas.

10. The process of claim 1, wherein at least a portion of the $C_{3-5}$ paraffinic feedstock is obtained from a cracked gas feed.

11. The process of claim 1, wherein at least a portion of the $C_{3-5}$ paraffinic feedstock is obtained from refinery waste gas treated to remove hydrogen, methane, ethane and olefins.

12. The process of claim 1, wherein the ethylene-rich product is isolated via fractional distillation.

13. The process of claim 1 wherein the dehydrogenation/hydrogenation catalyst includes at least one metal or a corresponding metal compound selected from the group consisting of iron, cobalt, nickel, ruthenium, rhodium, palladium, osmium, iridium, and platinum.

14. The process of claim 1 wherein the dehydrogenation/hydrogenation catalyst component comprises a noble metal or a compound thereof.

15. The process of claim 14 wherein the noble metal is platinum or palladium or a mixture of platinum and palladium or the compounds thereof.

16. The process of claim 14 wherein the dehydrogenation/hydrogenation component also contains a metal selected from the group consisting of rhenium, tin, germanium, gallium, indium, lead, tin, compounds thereof, and mixtures thereof.

17. The process of claim 1 wherein the olefin metathesis catalyst comprises a metal or corresponding metal compound selected from the group consisting of tungsten, molybdenum, tin or rhenium.

18. The process of claim 1, wherein the olefin metathesis catalyst comprises tungsten.

19. The process of claim 1 wherein the dehydrogenation/hydrogenation catalyst includes platinum or a platinum compound and the olefin metathesis catalyst includes tungsten or a compound of tungsten.

20. The process of claim 19 wherein the dehydrogenation/hydrogenation catalyst is a mixture of platinum-on-alumina and the olefin metathesis catalyst is tungsten-on-silica and the volumetric ratio of the platinum component to the tungsten component is greater than 1:50 and less than 50:1 and wherein the amount of platinum on the alumina is within the range of from about 0.01 weight percent to about 10 weight percent on an elemental basis and the amount of tungsten on the silica is within the range of from about 0.01 weight percent to about 50 weight percent on an elemental basis.

21. The process of claim 20 wherein the volumetric ratio of the platinum component to the tungsten component is between 1:10 and 10:1 and wherein the amount of platinum on the alumina is within the range of from about 0.1 weight percent to about 5.0 weight percent on an elemental basis and the amount of tungsten on the silica is within the range of from about 0.1 weight percent to about 20 weight percent on an elemental basis.

* * * * *

UNITED STATES PATENT AND TRADEMARK OFFICE
CERTIFICATE OF CORRECTION

| | | |
|---|---|---|
| PATENT NO. | : 6,441,263 B1 | Page 1 of 1 |
| APPLICATION NO. | : 09/612045 | |
| DATED | : August 27, 2002 | |
| INVENTOR(S) | : Dennis J. O'Rear et al. | |

It is certified that error appears in the above-identified patent and that said Letters Patent is hereby corrected as shown below:

Change page 1 as follows:

(73) Assignee: replace "ChevronTexaco Corporation, San Ramon, CA (US)" with --Chevron U.S.A. Inc., San Ramon, CA (US)--.

Signed and Sealed this

Twenty-second Day of August, 2006

JON W. DUDAS
*Director of the United States Patent and Trademark Office*